US006983106B2

(12) United States Patent
Van Houten

(10) Patent No.: US 6,983,106 B2
(45) Date of Patent: *Jan. 3, 2006

(54) SYNCHRONIZER FOR FUNDUS CAMERA

(75) Inventor: Peter A. Van Houten, Greenville, NC (US)

(73) Assignee: EyeExpert, LLC, Greenville, NC (US)

( * ) Notice: Subject to any disclaimer, the term of this patent is extended or adjusted under 35 U.S.C. 154(b) by 84 days.

This patent is subject to a terminal disclaimer.

(21) Appl. No.: 10/162,429

(22) Filed: Jun. 3, 2002

(65) Prior Publication Data
US 2003/0048412 A1 Mar. 13, 2003

Related U.S. Application Data

(63) Continuation-in-part of application No. PCT/US00/32554, filed on Nov. 30, 2000.

(30) Foreign Application Priority Data
Jun. 7, 2001 (WO) .................................... WO01/39661

(51) Int. Cl.
A61B 3/14 (2006.01)

(52) U.S. Cl. ..................... 396/18; 396/180; 396/205; 351/206

(58) Field of Classification Search ................... 396/14, 396/17, 18, 180, 189, 205, 206; 351/206; 348/64, 78, 370, 371
See application file for complete search history.

(56) References Cited

U.S. PATENT DOCUMENTS

| 5,504,542 A | 4/1996 | Hino et al. ................. 351/206 |
| 6,158,864 A | * 12/2000 | Masuda et al. ............. 351/206 |
| 6,361,167 B1 | 3/2002 | Su et al. ..................... 351/206 |

FOREIGN PATENT DOCUMENTS

DE 41 22 752 A1 1/1993

OTHER PUBLICATIONS

European Search Report for EP 0025.0415.7; Dated Feb. 27, 2003.

* cited by examiner

Primary Examiner—W. B. Perkey
(74) Attorney, Agent, or Firm—Myers Bigel Sibley & Sajovec, PA.

(57) ABSTRACT

A synchronizer is provided to establish a mechanical switching interface between an electronic digital color camera and a fundus camera for appropriately coordinating the complete opening of the color camera shutter with the energization of fundus camera flash unit, and for fully disconnecting the flash unit at the completion of an image capture sequence thereby enabling resetting of the flash unit.

29 Claims, 7 Drawing Sheets

SYNCHRONIZER FOR FUNDUS CAMERA

CROSS-REFERENCE TO PRIORITY APPLICATIONS

This application is a continuation-in-part of PCT application Ser. No. PCT/US00/32554, filed on Nov. 30, 2000, published in English as International Publication No. WO01/39661 A1 on Jun. 7, 2001, and claims priority to U.S. Provisional Patent Application No. 60/331,184, filed Nov. 9, 2001, the entire disclosures of which are incorporated herein by reference.

FIELD OF THE INVENTION

The present invention relates to cameras for the diagnosis of retinal disease, and, in particular to a system for synchronizing the flash unit of a monocular retina camera with a digital camera system.

BACKGROUND OF THE INVENTION

In the practice of ophthalmology and retinology, the ability to graphically view a patients retinal area under varying conditions is extremely beneficial in the clinical diagnosis of various disorders. One type of such camera, the fundus camera, is a three-axis camera providing photographic recording of a diversity of recognized fundus; presentation modes. The system also provides for black and white digital image recording, editing and archiving. Using highly corrected optical systems, brilliant imaging and high resolution is provided at the base of the retina suitable for clinical diagnosis. Most current cameras are also able to provide documentation of findings through photographic equipment, electronic image sensors and other options.

Fundus cameras are provided with a main black and white camera unit 20 mounted at the bottom camera port. During diagnosis, the clinician may use the main camera to compile a series of images for later diagnosis and documentation, and such activity is a mainstay feature of such units. The main-I-camera is operated from a joystick used to universally position the optics relative to the patient by depressing an actuator button at the top thereof. In such mode, the fundus camera optics and shutter system are activated for a predetermined time interval. When a signal to the fundus camera is received, the flash unit is activated to properly expose the film. If a signal is not received in such time interval, the fundus shutter system closes preventing image capture.

Oftentimes, it is desirable to supplement the black and white photographs with color photographs to enhance the diagnosis and documentation. Accordingly, the fundus camera is provided with a second camera port for the mounting and operation of a mechanical color camera. The operator can interface the color camera with the fundus camera through a connector harness for actuating the color camera from the joystick button. The system is effective in obtaining color exposures for subsequent development, printing and review. This can result is a significant time interval between examination and review of the color photographs.

With the advent of digital color cameras, there has been a pronounced interest at the clinical level to interface a digital color camera with the fundus camera. Such a combination would provide high quality, readily available color photographs for concurrent evaluation and diagnosis at the time of examination, as well as electronic storage for documentation and archiving. While widely accepted for many photographic purposes, the integration with the fundus camera has posed substantial problems, which heretofore have prevented effective use in the clinical practice.

Initial digital color cameras incorporated a mechanical electrical contact at the shutter that interfaced with a timing circuit of the flash unit to coordinate the flash sequence at the fully open shutter positions of both cameras. Certain difficulties were apparently created by the proprietary circuitry operating at the flash unit interface. The digital camera appears to incorporate a circuit board that requires a warmup interval before the shutter activation system on the digital camera can be operated. In ordinary usage, this is accommodated at an intermediate shutter button position wherein the circuit board is enabled, the shutter conditioned for release and the focusing system activated. In the fundus camera, the joystick button effectively bypasses the intermediate position. Accordingly, the signal to the flash unit is subject to two preconditions; the circuit warmup time and the mechanical shutter transit time. These two intervals exceed the aforementioned time interval for the fundus flash unit and the fundus shutter system closes before image capture.

The foregoing digital interface problem has been exacerbated by electronic digital cameras that have substantially replaced the mechanical versions. The latter version appears to have replaced the mechanical shutter contact with a non-publicly available electronic package. In normal operation, the mechanical shutter actuation button has two distinct, sequential positions to capture the images. In the first, partially depressed position, the main circuits are powered, the shutter is released for actuation, and the self-focusing mechanism initiated. In the second, fully depressed position, the shutter is released. The flash circuitry includes a delay to initiate the flash at 3 the fully open shutter condition. For most applications, quality digitized images may be captured and archived.

Nonetheless, integration of the electronic digital color camera with the fundus camera has presented difficulties beyond those experienced with the mechanical version. In the fundus camera, the joystick release button is a two-position switch that bypasses the aforementioned three-position sequential button on the camera body. When interfaced, the apparent circuitry of the camera does not synchronize the flash with the shutter, generally capturing an image in the partially opened shutter condition. This appears to result from an inherent circuitry warmup time required prior to the shutter opening sequence. Manual actuation with the internal switch, fast or slow, provides sufficient staging time to allow the circuitry to operate in synchronization whereas the fundus, camera sequence results in a time lag at the shutter unacceptably affecting the resultant image. Moreover, the problem of not resetting the flash unit persists. The flash units used in fundus cameras typically require full discharge and voltage interruption to allow the power supply to reset for the next exposure. The circuitry, the details of which are not publicly available, employed in such electronic digital cameras appear to provide a sufficient residual voltage preventing the flash unit from resetting. In order to make this interface operable, the operator would have to toggle the power supply at the main switch for recycling the flash unit. Understandably, such manipulation is undesirable and laborious inasmuch as a typical examination entails a substantial number of images for capture.

Notwithstanding the foregoing problems, the desire and need at the clinician level to secure high quality digital color images on the fundus camera persists.

Accordingly, it is an object of the present invention to provide an interface between a fundus camera and a digital color camera for providing proper exposure of desired images.

Another object of the present invention is to provide an interface between a fundus, camera and a digital color camera flash control that will effect resetting of the fundus camera flash unit after each exposure.

A further object is to provide synchronization between shutter opening on a digital color camera and the flash unit of a fundus camera.

A still further object is to provide a synchronizing interface between a fundus camera and an electronic digital color camera not requiring structural modification of either camera.

Yet another object is to coordinate the shutter systems of a digital color camera and a fundus camera to provide a quality focused exposure in synchronization with the flash unit on a fundus camera.

SUMMARY OF THE INVENTION

The foregoing objects are accomplished by a synchronizer in accordance with the invention wherein a mechanical switching interface is provided between an electronic digital color camera and a fundus camera for appropriately coordinating the complete opening of the color and fundus camera shutters with the energization of the fundus camera flash unit, and for fully disconnecting the flash unit at the completion of an image capture sequence thereby enabling resetting of the flash unit. More particularly, the synchronizer comprises a pair of control circuits, each of which includes a mechanical relay. In a first circuit, at startup, the main circuitry and the focusing unit are continuously operated, and the shutter lock mechanism released. This configuration eliminates the system warmup time lag, provides continuous focusing, and conditions the shutter system for opening. In the second circuit, the lamp unit is conditioned for operation. Accordingly, upon depressing the fundus camera switch, the shutter release mechanism is actuated, the shutter openings for both cameras coordinated within the fundus prescribed interval corresponding to the fully open shutter positions, the flash unit is actuated, and thereafter the shutter mechanism is reset. Upon release of the fundus camera switch the circuit to the flash unit is mechanically interrupted allowing automatic resetting thereof. The use of the relays in both circuits nullifies the influence of the relay switching times insuring that the built in predetermined camera delay time remains matched at time of flash. The foregoing is achieved without revision of the digital camera or the fundus camera, through simple and readily available components, to achieve thereby the stated objectives.

An object of the present invention is to provide a flash and photograph synchronizer for a fundus camera having an actuator, a resettable flash unit accommodating a flash sequence in a flash interval after actuation of the actuator and requiring power interruption thereto for resetting, and a digital camera system including an auxiliary power supply and a shutter system having a mechanical shutter movable to a fully open position in the mechanical transit time consistent with the flash interval for capturing an image at the digital camera system, the synchronizer comprising a power supply means, a first circuit means including a first mechanical switching means for operatively connecting the auxiliary power supply with the shutter system upon operation of the actuator moving the mechanical shutter to a fully open position, and a second circuit means including a second mechanical switching means connected between the power supply means and tile flash unit for actuating the flash unit upon operation of the actuator to initiate the flash sequence during the flash interval, the second mechanical switching means effecting power interruption to the flash unit subsequent to the operation of the actuator thereby permitting the resetting thereof.

A further object of the invention is to provide a synchronizer for a fundus camera for coordinating an auxiliary digital camera to record an image in timed sequence with a fundus camera actuator and a flash unit coupled to the fundus camera, the digital camera including a power supply connected to a circuit board coupled with a shutter system; comprising a first means for normally enabling the circuit board, and a second means responsive to operation of the fundus camera actuator for conditioning the shutter system at a fully open position and energizing the flash unit, subsequent to operation of the fundus camera actuator interrupting power to the flash unit.

A further object of the invention is a method for synchronizing image capture between a digital camera and a flash unit operatively coupled to a fundus camera wherein the digital camera includes a circuit board coupled to a power supply and a shutter system, the shutter system is movable from a shutter activation position to a fully open position for capturing the image, and the flash unit includes means for energizing the flash unit and preventing subsequent energizing thereof in the absence of cessation of power thereto comprising the steps of:

(a.) normally connecting the circuit board to the power supply;

(b.) activating the shutter system to the fully open position; and, (c.) subsequent to the activating, effecting cessation of power to the flash unit and returning the shutter system to the shutter activation position.

In a further object of the invention, in a fundus camera for recording an image from a camera port upon operation of an actuator switch having a first position and a second position, a camera system comprising a flash unit including a main power supply operatively coupled to the fundus camera, the flash unit including control means for providing illumination in response to a signal received within a predetermined time interval and precluding subsequent illumination until cessation of power to the control means; an electronic digital camera operatively coupled to the camera port, the digital camera including an auxiliary power supply coupled to a circuit board and to a shutter system, the shutter system movable responsive to operation of the actuator switch from a first position to a My open position in a mechanical transit time less than the predetermined time interval, the digital camera providing an output signal after the mechanical transit time; a synchronizer including a switchable power supply and a first circuit means and a second circuit means, the first circuit means connected to the power supply, the circuit board and the shutter means for normally powering the circuit board the first circuit means including a switching device having a first switching time, the second circuit means including a second switching device having a second switching time generally the first switching time, the second switching device effective for providing a cessation of power in the second circuit means in the first position of the actuator.

A further object of the invention, a synchronizer for coordinating a fundus camera flash unit with a digital color camera wherein the flash unit requires an enabling flash signal within a predetermined time interval after actuation and the color camera includes circuitry requiring a warmup time after actuation and a shutter transit time less than the predetermined time interval after the warmup time to transmit the flash signal, the warmup time and the shutter transit time exceeding the predetermined time interval, the synchronizer comprising a switchable power supply means normally operatively connected to the flash unit and the circuitry of the digital color camera thereby normally powering the circuitry and eliminating the warmup time such that the flash signal is received at the flash unit within the predetermined time interval.

DESCRIPTION OF THE DRAWINGS

The above and other objects and advantages of the present invention will become apparent upon reading the following detailed description taken in conjunction with the accompanying drawings in which.

DETAILED DESCRIPTION OF EMBODIMENTS ACCORDING TO THE INVENTION

Figure 1:
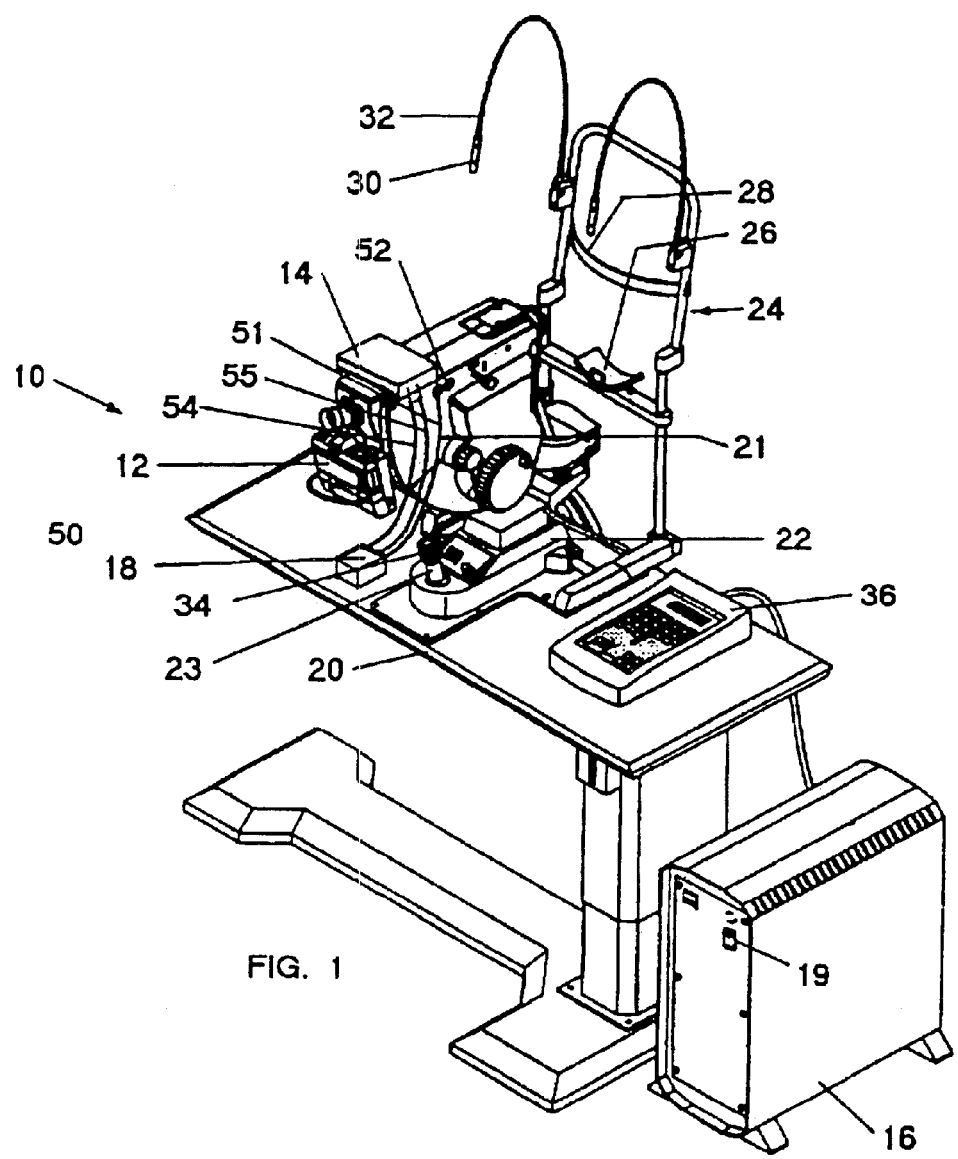
FIG. 1 is a perspective view of a fundus camera carrying a digital camera interfaced with a synchronizer in accordance with the invention.

Referring to the drawings for the purpose of describing the preferred embodiment, FIG. 1 illustrates a fundus camera (FC) 10, also known as a monocular retina camera, having a first camera 12 optically coupled thereto at a main camera port at the rear thereof, and a second camera 14, an electronic digital color camera (DCC), optically coupled thereto at an auxiliary camera port at the top thereof. The fundus camera 10 also includes a flash unit 16 coupled thereto for providing flash illumination in coordination with the cameras for capturing and recording patient information during an examination. A synchronizer 18 is interfaced between the fundus camera 10 and the digital color camera 14 by wiring harness 21.

For the purpose of the present embodiment, the fundus camera may be selected from a plurality of commercially available models. A suitable fundus camera is available from Carl Zeiss Jena GmbH of Jena Germany as model FF 450. Similarly, the digital color camera may be selected from commercially available models. A suitable digital color camera is available from Eastman Kodak Company as an adjunct to the Professional Digital Camera System, in particular a modified Nikon F3 camera body.

Both the fundus camera 10 and the digital camera 14 incorporate proprietary, non-publicly available circuitry for performing certain functions in accomplishing the objectives of the invention. The following description will accordingly proceed with reference to the synchronizer interface with such functions, it being understood that those skilled in the art be able to determine the necessary specifics for integrating the selected camera.

More particularly, the fundus camera 10 is a monocular retina camera for routine clinical and diagnostic usage. The fundus camera 10 is fixedly mounted on an instrument table 20 having a motorized height adjustment, not shown. The main camera 12 may comprises a Nikon F3-HP type. The fundus camera 10 is universally coupled with an instrument base 22 including a 3D joystick 23 for universally positioning the camera optics with respect to a patient presenting for examination at a vertically adjustable head rest 24 including a vertically adjustable chin rest 26 and a forehead rest 28. Fixation lights 30 mounted on flexible necks 32 are used conventionally in the diagnosis and examination. The joystick 23 includes a camera button 34 on the top thereof for initiating a camera exposure session. A control console 36 operates in conjunction with the camera to control various functions ancillary to the present invention.

The fundus camera is also provided various mechanical controls for focusing, tilting and otherwise allowing the clinician to observe readily and accurately the desired retinal areas of the patient.

The digital camera 14 is mounted on the top optical port of the camera and may be selected for operation by controls, not shown. The synchronize 18 comprises a housing 50 mounted on the table 20 or other suitable location having an connector cable 51 coupled with the camera port 52 on the fundus camera and cables 54, 56 connected to the main camera port and the flash port. The camera 14 is operatively connected to a digital storage unit by a supplied connector cable, not shown. The internal circuitry for the fundus camera is power by a power supply resident in the flash unit 16. Subject to the incorporation of the synchronizer of the present invention, the fundus camera is operable for clinical and diagnostic purposes in a manner well known by those in the art.

An illustrative digital color camera for the purposes of the present invention is an unmodified Nikon F3 camera fitted with a Kodak camera back and camera winder connected to a free standing digital storage unit by an interconnect cable. As can best be ascertained for describing the preferred embodiment the digital camera includes a control system including a main circuit board, a focusing system, a shutter system, and a flash system. Images are normally captured by a manual two-position button. In the first partially depressed position, the control system is enabled thereby enabling the circuit board, the focusing system, and the shutter system to a shutter activation position. Sequentially thereafter, in the second fully depressed position, the shutter system releases the shutter blades and, at the fully open position, sends a signal to the associated flash system. In the fundus camera flash system, the shutter system is enabled and the optics and shutter opened for a preset interval awaiting an actuation flash signal. This interval is consistent with the mechanical transit time of the digital camera shutter.

In normal usage, the shutter button is depressed in stages by the operator in a well known manner. Sufficient time is thus presented for the main circuit to warmup and for the control system to condition fully and the focusing system to align accurately with the photographic subject. Subsequent full depression of the button will thus establish the proper time interval between full shutter opening and flash unit energization. Normally, even if the operator depresses the button in a single motion sufficient staging time is effected for appropriately coordinating shutter and flash functions. However, the one stage actuation of the fundus camera button does not provide sufficient warmup time, resulting in a flash signal exceeding the fundus camera shutter opening interval thereby precluding image capture.

Figure 5:
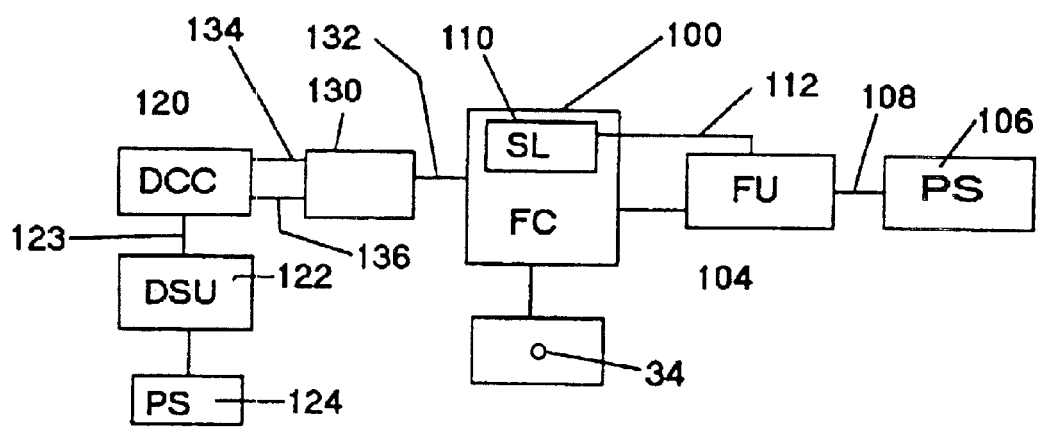
FIG. 5 is a block diagram of the synchronizer operation.

Referring to FIG. 5, there is illustrated a block diagram for the present invention for overcoming the aforementioned limitations in the interface between the digital camera and the fundus camera. Therein, the fundus camera 100 is operatively connected to the flash unit 102 by connector cable 104. The flash unit 102 is connected to external power supply 106 by cable 108 and to the flash strobe light 110 resident inside the fundus camera 100 by cable 112. The fundus camera imaging is effected by the joy stick switch or button 34.

The digital camera 120 is connected to digital storage unit 122 by cable 123 and to a internal power supply 124 therein. The synchronizer 130 is coupled to the fundus camera by inlet cable 132, to the flash system of the digital camera 120 by outlet cable 134 and to the camera control system by outlet cable 136.

Figure 2:
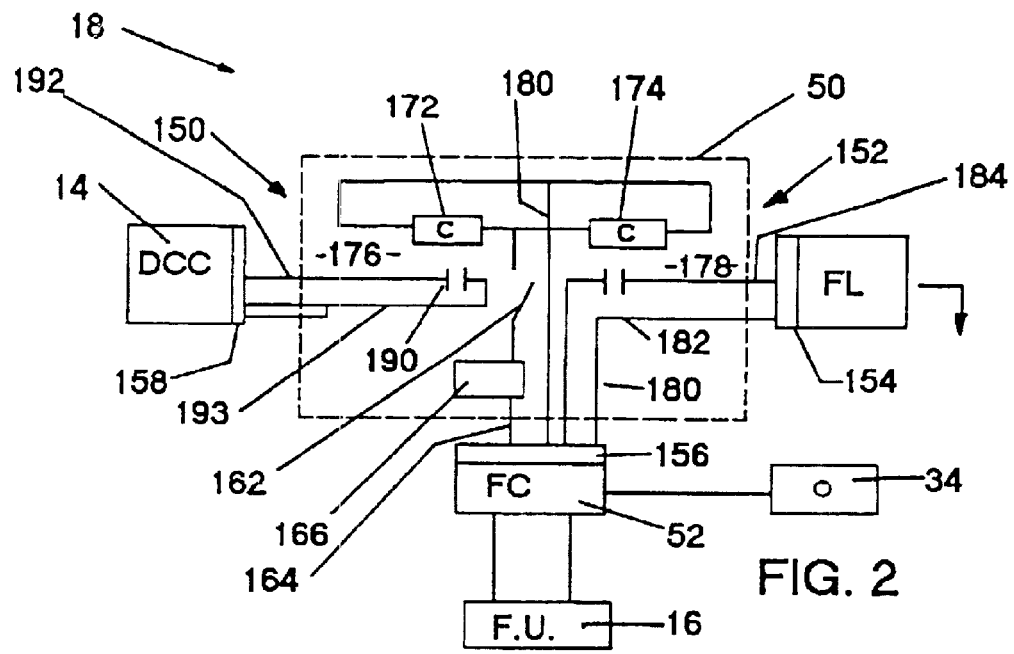
FIG. 2 is a schematic diagram of the synchronizer interfaced with the fundus camera and the digital camera.

More particularly and as shown in the schematic diagram of FIG. 2, the synchronizer 18 comprises a pair of switching circuits 150, 152 for overriding existing internal controls, and operating and coordinating the shutter opening and flash sequencing between the fundus camera and the digital camera. The first switching circuit 152 is coupled to flash connector 15 154 mounted on the digital camera and to the auxiliary connector 156 for the auxiliary camera port 52 on the fundus camera. The second switching circuit 150 is coupled to the main camera connector 158 on the digital camera and the connector 156 on the auxiliary camera port on the fundus camera.

The synchronizer 18 comprises a main switch 162 connected by lead 164 to a direct current power supply 166 and the auxiliary port connector 156 on the fundus camera. The power supply 166 is connected in parallel to the coils 172, 174 of normally open relays 176, 178 respectively. The coils 172, 174 are connected to ground at the fundus camera by lead 180 at the port connector 156. The normally open contacts 182 of the relay 178 are connected by lead 184 to the flash system port connector 154 on the digital camera. As discussed below, closure of the joystick button 34 on the fundus camera will activate the relay 178 closing contacts 182 completing the circuit to the digital camera flash system via lead 188 between the connector 154 and port connector 156. Leads 184 and 188, and port connector 156 comprise the outlet cable 56.

Figure 3:
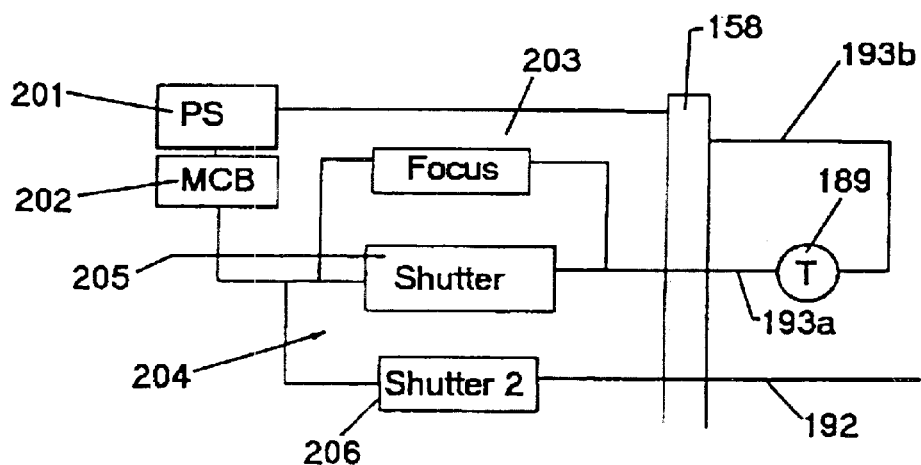
FIG. 3 is a schematic diagram of the digital camera control system.

The contacts 190 of relay 176 are connected by leads 192, 193 to the shutter port connector 158 on the digital camera. Lead 193 includes branch leads 193a and 193b at the connector 194. The leads 192, 193 and connector 158 comprise outlet cable 54 (FIG. 3). The leads 180, 184, 164 and 188 and the connector 158 comprise the outlet cable 51 from the synchronizer housing 50. Timing means 189 may be incorporated, as in line 193, to deactivate the above functions after a predetermined time.

Referring to FIG. 3, leads 193a and 193b are connected to the storage unit power supply 201, the main circuit board 202, the focus system 203 and shutter system 204. Consequently, as described below, the circuit board, the focusing system and first stage are continuously powered. Lead 192 is connected with the shutter system 204 such that contact closure activates the mechanical release of the shutter and sends an enabling signal 206 to the digital camera flash system at the fully open position, to the plug connector 154 and lines 188, 184 in switching circuit 152.

The flash system of the fundus camera to the extent known appears to incorporate a shutter system for conditioning the optics and opening the shutter to receive within a preset time interval after actuation of the joystick button 34 such that the flash is in proper sequence with the fully open shutter position. Upon closure of contacts 190, the flash signal will be transmitted to the auxiliary port 52 a predetermined time thereafter. Moreover, it appears that the flash system of the digital camera includes circuitry presenting a residual voltage to the flash unit of the fundus camera through details not present known, sufficient to prevent the resetting of the fundus camera flash unit. Accordingly, the opening of the contacts 182 mechanically interrupts power to the flash unit permitting the resetting thereof.

Lead 192 of shutter connector 158 is connected to the power supply 201 of the digital storage unit. Lead 193a appears to be connected to the circuit board 202 and the system 203. Accordingly the latter systems operate continuously until timed out by timer 189 in the synchronizer 18. When the contacts 190 are closed the second shutter is released for timed coordination with the flash unit. It will be appreciated further that the dual relays in the separate circuits have the effect of balancing the switching times associated with the individual relay, thereby retaining the predetermined time intervals between shutter opening and flash provided by the camera manufacturers. Further, by locating the contacts in an independently powered circuit, the existing camera functions operate on design voltage.

For the Nikon camera of the preferred embodiment, lead 193b is connected to pin 10, lead 193a to pin 4 and lead 192 to pin 7.

Figure 4:
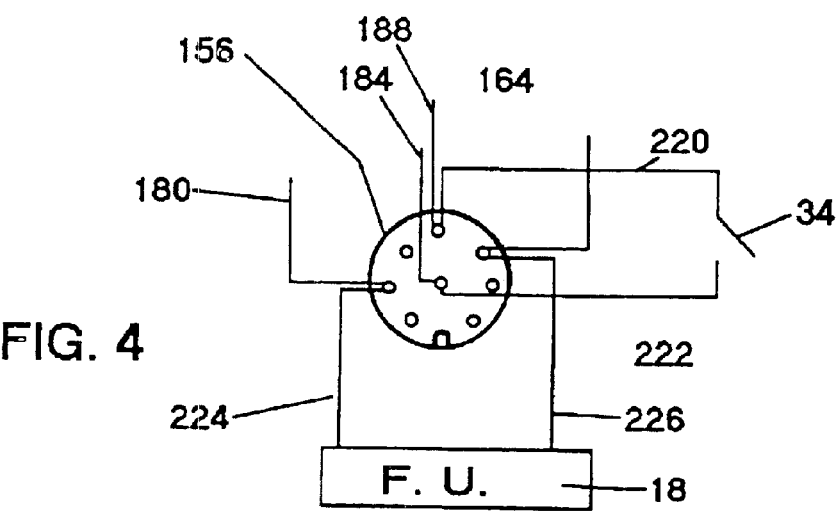
FIG. 4 is a schematic diagram of the fundus camera flash control system.

Referring to FIG. 4, the fundus camera connector 156 interfaces with the auxiliary port 52 and is connected with the joystick button 34 through internal leads 220 and 222. The internal leads 224 and 226 are connected with the flash unit 16. For the Zeiss FF449 fundus camera, leads 180, 224 are connected to pin 2, leads 164, 226 to pin 5, leads 222, 184 to pin 8 and leads 220, 188 to pin 4.

Referring to FIGS. 2 and 5, in operation, with the main power switches to the flash unit 16 and the digital storage unit closed, and the synchronizer connected, the circuit board and focusing system are powered. When the clinician desires to capture a digital color image, the appropriate mode is selected on the fundus, camera controls. Thereafter, the desired image area is selected and the joystick button 34 is depressed. Thereupon the relays 178, 176 are energized closing the contacts 182, 190. After contact closure, the shutter mechanism is actuated to initiate opening of the shutter blades. At the fully open position, the flash system circuit is completed to fire the flash unit in the fundus camera in proper sequence with fully shutter opening of both cameras thereby capturing a synchronized image for filing in the storage system. After shutter opening the winding mechanism is activated to rewind the film and mechanically reset the shutter mechanism. Upon release of the joystick button 34, the relays 176 and 178 are deenergized opening contacts 190 and 182. This results in a total cessation of power to the flash unit allowing the unit to reset for the next exposure.

The above embodiment has been described above with reference to a stand-alone synchronizer not requiring modifications to either camera. However, it will be appreciated that all or a portion of the functions may be integrated into either camera.

As will be appreciated by one of skill in the art, the present invention may be embodied as methods, systems, and/or computer program products. Accordingly, the present invention may take the form of an entirely hardware embodiment, an entirely software embodiment or an embodiment combining software and hardware aspects. Furthermore, the present invention may take the form of a computer program product on a computer-usable storage medium having computer-usable program code embodied in the medium. Any suitable computer readable medium may be utilized including hard disks, CD-ROMs, optical storage devices, or magnetic storage devices.

Computer program code or "code" for carrying out operations according to the present invention may be written in an object oriented programming language such as JAVA®, Smalltalk or C++. The code for carrying out such operations may also be written in conventional procedural programming languages, such as "C", JavaScript, Visual Basic, TSQL, Perl, or in various other programming languages. Software embodiments of the present invention do not depend on implementation with a particular programming language.

These computer program instructions may be stored in a computer-readable memory (such as a FLASHROM or other type of non-volatile memory) that can direct a computer or other programmable data processing apparatus to function in a particular manner, such that the instructions stored in the computer-readable memory produce an article of manufacture including instruction means which implement the function described.

Figure 6:
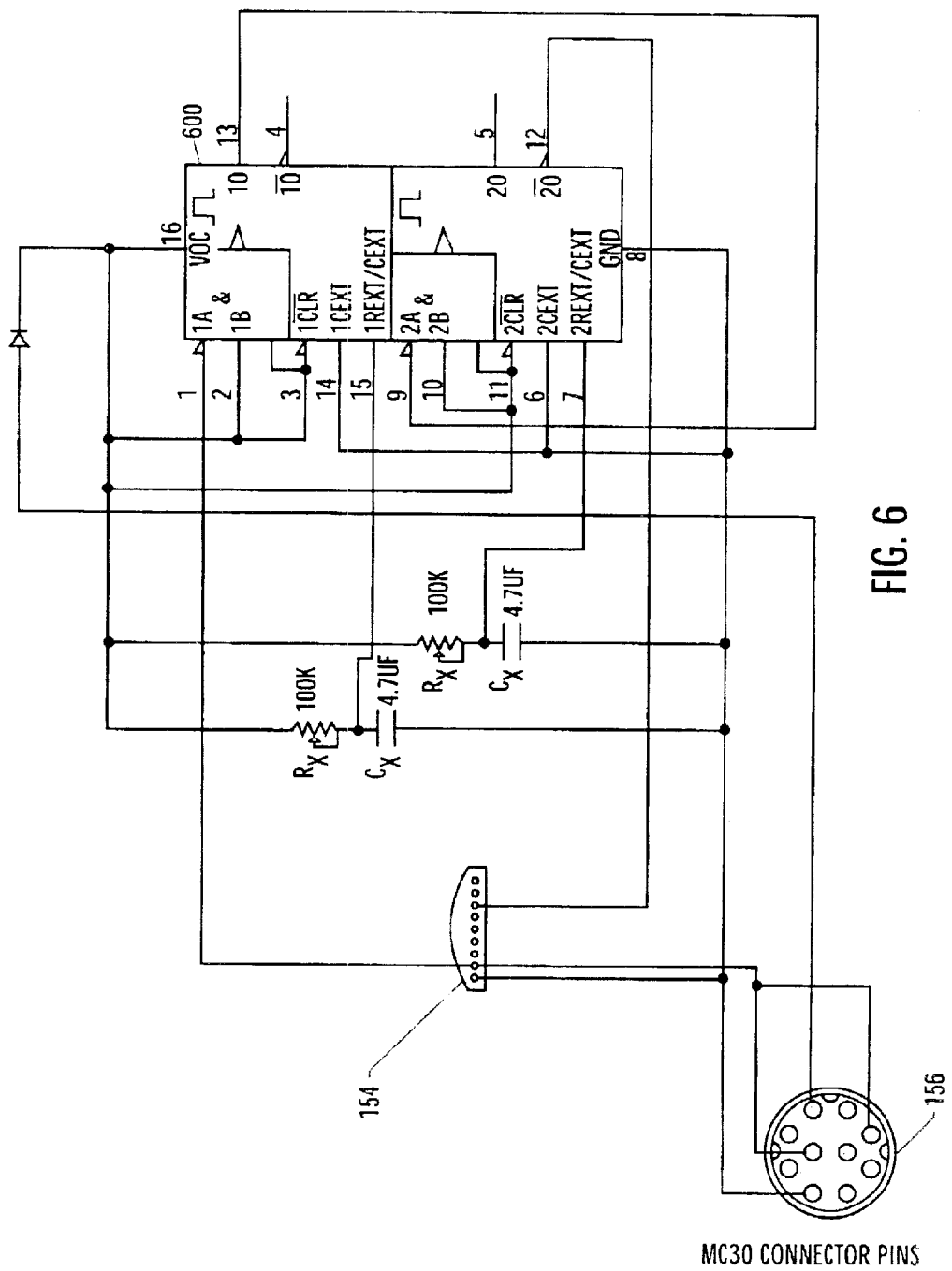
FIG. 6 is a circuit diagram that illustrates embodiments of synchronizer circuits according to the present invention.

In further embodiments according to the present invention as illustrated for example in FIG. 6, a monostable multi-vibrator 600 can generate a flash signal to interrupt the power to the flash unit 16 in the fundus camera. The monostable multi-vibrator can generate an output pulse of duration t determined by the value of the resistor RX and the capacitor CX connected to pin 15 of the monostable multi-vibrator 600.

Although the capacitors of the resistor RX and the capacitor CX are shown as having values 100 k and 4.7 $\mu$F respectively, it will be understood by those of ordinary skill in the art that other values may be used. For example, in further embodiments according to the present invention RX can be 5 k whereas the value of the capacitor CX is zero.

The monostable multi-vibrator 600 may be "retriggerable" such that further trigger pulses provided to the monostable multi-vibrator 600 cause the duration of the output pulse to be lengthened. For example, once triggered, the output pulse width may be extended by retriggering inputs $\overline{A}$ and B. The output pulse can be terminated by a low level on the reset pin. Trailing edge triggering ($\overline{A}$) and leading edge triggering (B) inputs are provided for triggering from either edge of the input pulse. Accordingly, the time at which power is interrupted to the flash unit 16 can be varied based on additional trigger pulses provided to the monostable multi-vibrator 600.

Figure 7:
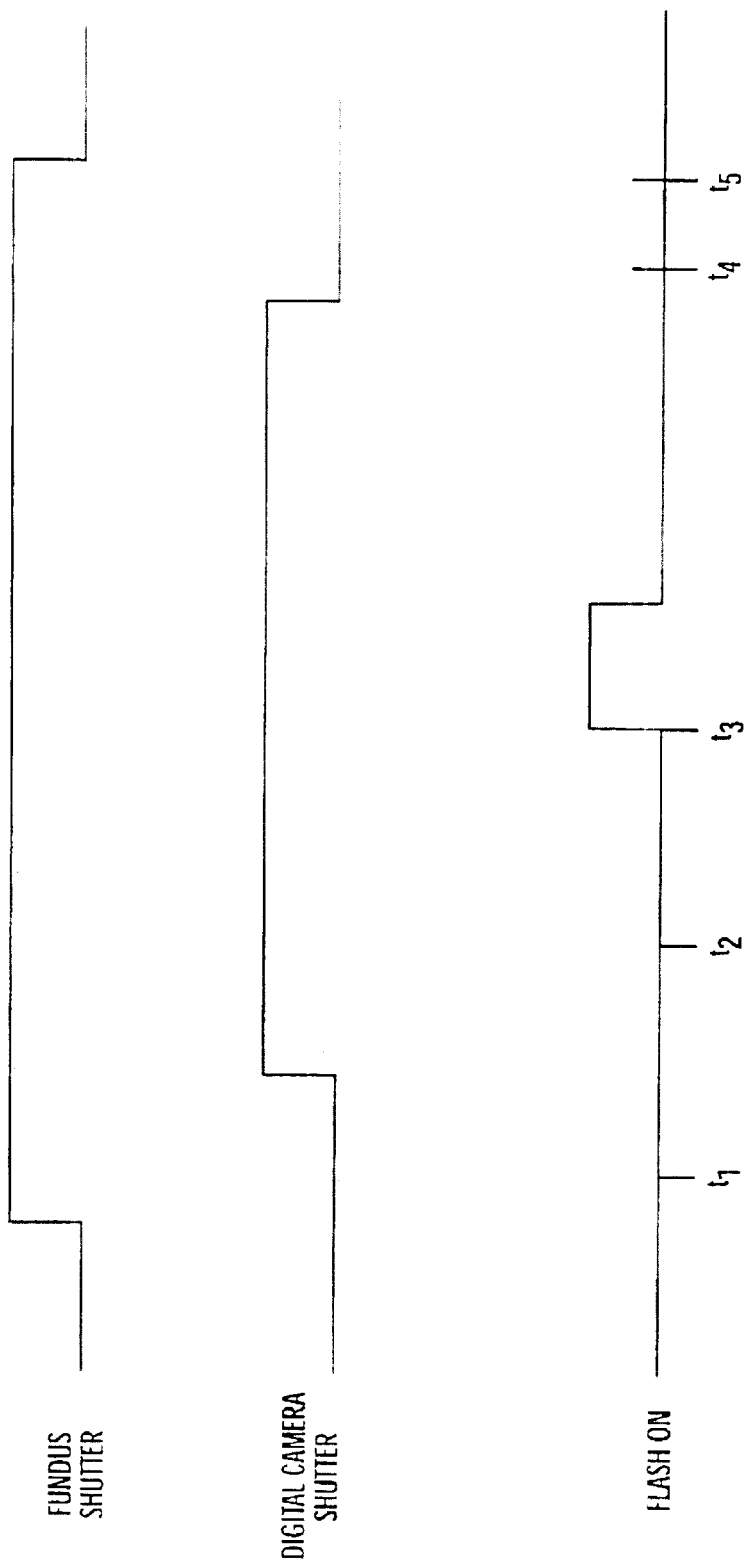
FIG. 7 is a timing diagram that illustrates operations of embodiments of synchronizer circuits according to the present invention.

FIG. 7 is a timing diagram that illustrates operations of embodiments according to the present invention. In particular, the shutter of the fundus camera opens at a time t1. Subsequently, the shutter of the digital cameral opens at a time t2. While the shutter of the fundus camera and the shutter of the digital camera are both open, the flash unit of the fundus camera is triggered by a flash on pulse at a time t3. The power to the flash unit is interrupted when the flash on signal is inactivated at a time t6. Furthermore, the pulse width of the flash on signal can also be variable. At a time t4 the shutter of the digital camera closes followed by the closing of the shutter of the fundus camera at t5. Also, the delay from the opening of the shutter of the digital camera to the activation of the flash of the fundus camera (i.e. t3–t2) may be variable.

Figure 8:
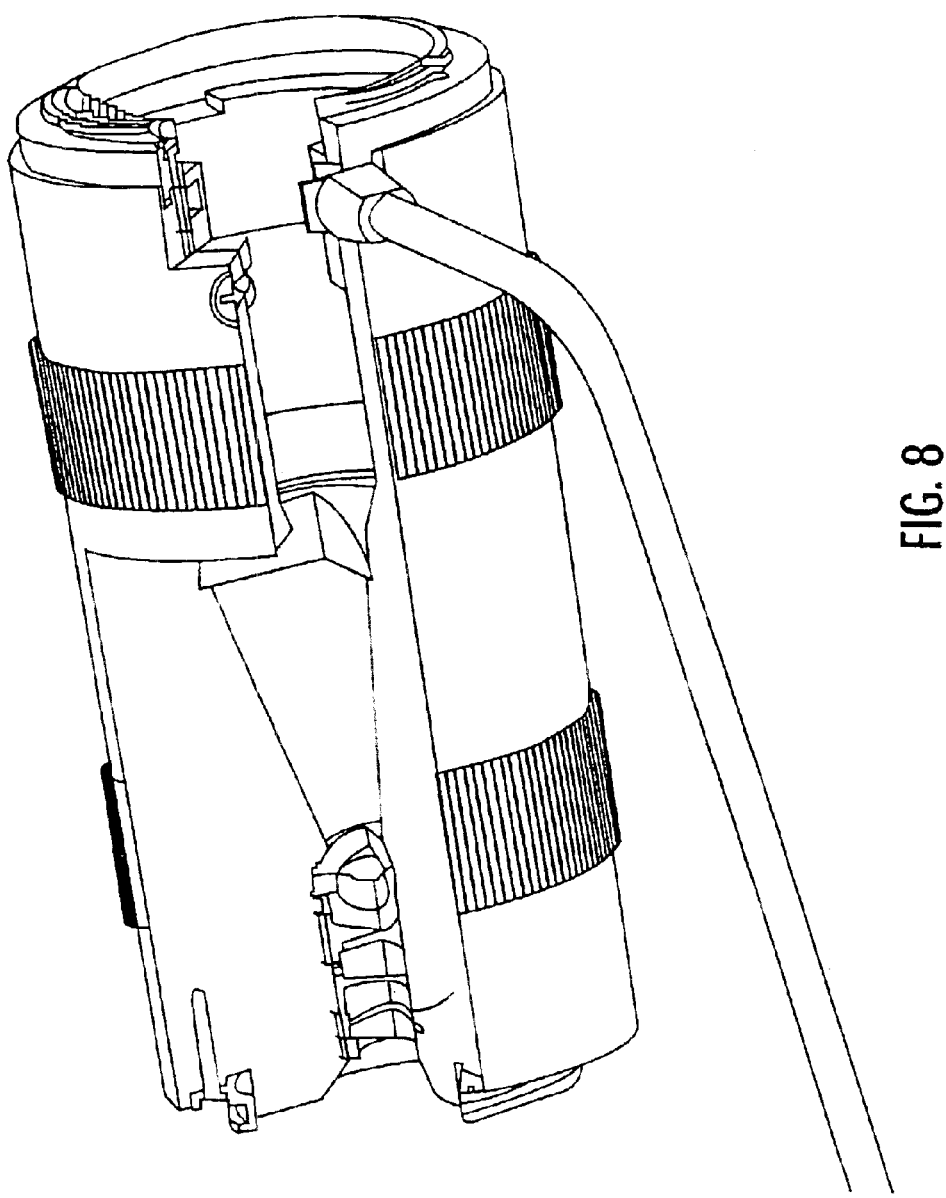
FIG. 8 is a circuit diagram that illustrates embodiments of synchronizer circuits according to the present invention.

In further embodiments according to the present invention, the synchronizer can be included in a housing along with optics to provide images from the fundus camera to the digital camera as shown, for example, in FIG. 8.

Figure 9:
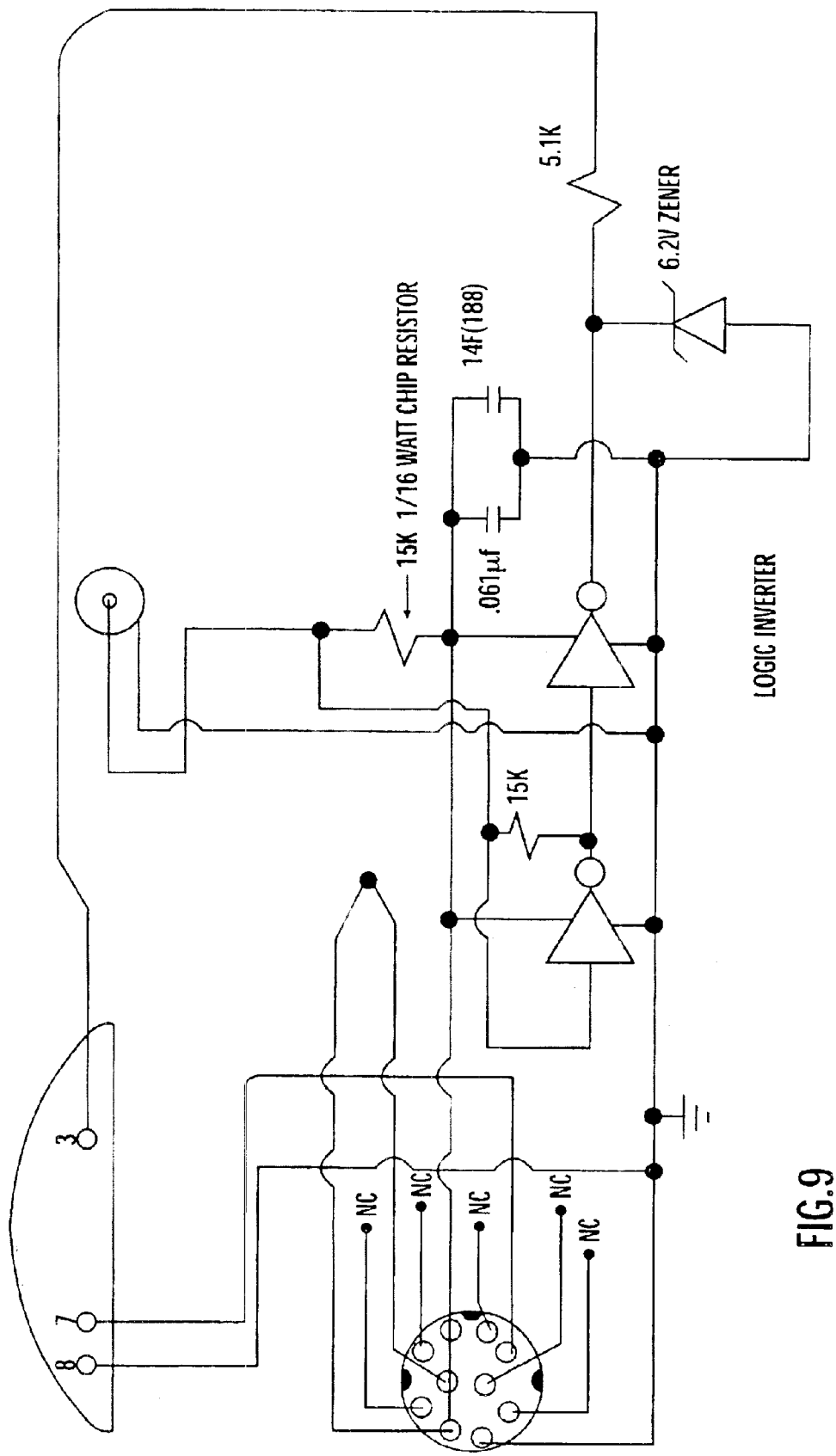
FIG. 9 is a schematic diagram that illustrates a transimpedence circuit according to some embodiments of the invention.

In still further embodiments according to the present invention, as illustrated by FIG. 9, a trans-impedance circuit is used to increase a voltage level of a sync pulse generated by the digital camera from about 0.0 to 0.7V to about 0.0 to 5.0V. An inverter inverts the modified sync pulse to provide a negative going pulse that is provided to the fundus camera flash unit soon after the digital camera is ready to sampled a digital image.

Having thus described a presently preferred embodiment of the present invention, it will now be appreciated that the objects of the invention have been fully achieved, and it will be understood by those skilled in the art that many changes in construction and widely differing embodiments and applications of the invention will suggest themselves without departing from the spirit and scope of the present invention. The disclosures and description herein are intended to be illustrative and are not in any sense limiting of the invention, which is defined solely in accordance with the following claims.

What is claimed is:

1. A synchronizer for a fundus camera for coordinating an auxiliary digital camera to record a image in timed sequence with a fundus camera actuator and a flash unit coupled to the fundus camera, the digital camera including a power supply connected to a circuit board coupled with a shutter system; comprising:

a circuit configured to enable the circuit board and configured to place the shutter system in an open position, energize the flash unit, and configured to interrupt power to the flash unit subsequent to operation of the fundus camera actuator responsive to operation of the fundus camera actuator.

2. The synchronizer of claim 1, wherein the flash unit operates according to a flash sequence in a flash interval after actuation of the actuator, the fundus camera configured to coupled to a digital camera system including an auxiliary power supply and a shutter system having a digital camera shutter having an associated open position in a transit time consistent with the flash interval to capturing an image at the digital camera system, the circuit further comprising:

a first circuit configured to operatively connect the auxiliary power supply with the shutter system upon operation of the actuator causing the digital camera shutter to the open position; and a second circuit configured to connect a power supply to the flash unit to actuate the flash unit upon operation of the actuator to initiate the flash sequence for the flash interval, the second circuit configured to interrupt power to the flash unit subsequent to the operation of the actuator to reset the flash unit for subsequent operation.

3. The synchronizer of claim 1 wherein the digital camera comprises a digital color camera wherein the flash unit accepts an enabling flash signal within a predetermined time interval after actuation and the color camera includes circuitry having an associated warmup time after actuation and a shutter transit time less than the predetermined time interval after the warmup time to transmit the flash signal, the warmup time and the shutter transit time exceeding the predetermined time interval, the synchronizer further comprising:

a switchable power supply operatively connected to the flash unit and the digital color camera configured to power the digital color camera and to reduce the warmup time such that the flash signal is received at the flash unit within the predetermined time interval.

4. The synchronizer of claim 1, wherein the fundus camera is coupled with an instrument base including a 3-D joystick for positioning the optics of the camera.

5. The synchronizer of claim 1, wherein the synchronizer includes a housing, and connector cables configured to connect to the camera and flash unit.

6. The synchronizer of claim 5, wherein the first circuit is coupled to a flash unit on the digital camera and to a connector on the fundus camera.

7. The synchronizer of claim 1, wherein the circuit is continuously powered.

8. A synchronizer for a fundus camera for coordinating an auxiliary digital camera to record a image in timed sequence with a fundus camera actuator and a flash unit coupled to the fundus camera, the digital camera including a power supply connected to a circuit board coupled with a shutter system; comprising:

first means for enabling the circuit board; and second means, responsive to operation of the fundus camera actuator, for placing the shutter system in an open position and energizing the flash unit, and for interrupting power to the flash unit subsequent to operation of the fundus camera actuator.

9. A synchronizer for a fundus camera for coordinating an auxiliary digital camera to record an image in timed sequence with a fundus camera actuator and a flash unit coupled to the fundus camera, the digital camera including a power supply connected to a circuit board coupled with a shutter system, wherein the flash unit operates according to a flash sequence in a flash interval after actuation of the actuator, the fundus camera configured to be coupled to a digital camera system including an auxiliary power supply and a shutter system having a digital camera shutter having an associated open position in a transit time consistent with the flash interval to capturing an image at the digital camera system, the synchronizer further comprising:

first means for operatively connecting the auxiliary power supply with the shutter system upon operation of the actuator causing the digital camera shutter to the open position; and second means configured to connect a power supply means to the flash unit to actuate the flash unit upon operation of the actuator to initiate the flash sequence for the flash interval, the second means causing power interruption to the flash unit subsequent to the operation of the actuator to reset the flash unit for subsequent operation.

10. The synchronizer of claim 9 wherein the first means comprises an electronic circuit.

11. The synchronizer of claim 9, wherein the first means comprises a mechanical switch.

12. The synchronizer of claim 9 wherein the second means comprises an electronic circuit.

13. The synchronizer of claim 9 wherein the second means comprises a mechanical switch.

14. The synchronizer of claim 9 wherein the digital camera shutter comprises a mechanical shutter.

15. The synchronizer of claim 9 wherein the digital camera comprises a digital color camera wherein the flash unit accepts an enabling flash signal within a predetermined time interval after actuation and the color camera includes circuitry having an associated warmup time after actuation and a shutter transit time less than the predetermined time interval after the warmup time to transmit the flash signal, the warmup time and the shutter transit time exceeding the predetermined time interval, the synchronizer further comprising:

switchable power supply means operatively connected to the flash unit and the digital color camera thereby powering the digital color camera and reducing the warmup time such that the flash signal is received at the flash unit within the predetermined time interval.

16. The synchronizer of claim 9, wherein the power supply means comprises a switchable power supply.

17. The synchronizer of claim 9, wherein the fundus camera is coupled to an instrument base including a 3-D joystick for positioning the optics of the camera.

18. The synchronizer of claim 9, wherein the synchronizer includes a housing, and connector cables the cables being configured to connect to the camera and flash unit.

19. The synchronizer of claim 9, wherein the first means is coupled to a flash unit on the digital camera and to a connector on the fundus camera.

20. The synchronizer of claim 9, wherein the first and second means are continuously powered.

21. A method for synchronizing image capture between a digital camera and a flash unit operatively coupled to a fundus camera wherein the digital camera includes a circuit board coupled to a power supply and a shutter system, the shutter system being movable from a shutter activation position to an open position for capturing the image, and the flash unit includes means for energizing the flash unit and avoiding subsequent energizing thereof, the method comprising the steps of:

connecting the circuit board to the power supply;

activating the shutter system to the open position; and then interrupting power to the flash unit and returning the shutter system to the shutter activation position.

22. A synchronizer for a fundus camera for coordinating operation of a digital color camera with an exposure generated by a fundus camera including a fundus camera shutter and coupled to a flash unit to record an image via the digital color camera, the digital color camera including a digital color camera circuit coupled with a digital color camera shutter system, the synchronizer comprising:

a circuit responsive to operation of the fundus camera configured to place the digital color camera shutter system in an open position and configured to energize the flash unit at a time when the digital color camera shutter system and the fundus camera shutter are in respective open positions, the circuit being further configured to temporarily reset power to the flash unit subsequent to operation of the fundus camera.

23. A synchronizer according to claim 22 wherein the synchronizer is enclosed in a synchronizer housing that is outside the fundus camera and outside the digital color camera.

24. A synchronizer according to claim 22 wherein the circuit comprises:

a first switching circuit configured to electrically couple the fundus camera to the digital color camera to activate the digital color camera shutter system responsive to a user input at the fundus camera.

25. A synchronizer according to claim 24 wherein the first switching circuit further comprises:

a first relay configured to close contacts therein to activate the digital color camera shutter system.

26. A synchronizer according to claim 25 wherein the first switching circuit further comprises:
   a timer circuit configured to electrically decouple the digital color camera shutter system from the synchronizer after a predetermined timer circuit interval to de-activate the digital color camera shutter sytem.

27. A synchronizer according to claim 24 wherein the circuit further comprises:
   a second switching circuit configured to electrically couple a signal generated at the digital color camera ater a predetermined digital color camera flash warm-up interval responsive to activation of the digital color camera shutter system.

28. A synchronizer according to claim 27 wherein the second switching circuit is further configured to interrupt power to the flash unit by electrically decoupling the signal generated at the digital color camera from the flash unit to reset the flash unit for subsequent use.

29. A synchronizer according to claim 27 wherein the second switching circuit further comprises:
   a second relay configured to close/open contacts therein to electrically couple/decouple the flash unit to the digital color camera.

* * * * *

UNITED STATES PATENT AND TRADEMARK OFFICE
CERTIFICATE OF CORRECTION

PATENT NO. : 6,983,106 B2
APPLICATION NO. : 10/162429
DATED : January 3, 2006
INVENTOR(S) : Van Houten It is certified that error appears in the above-identified patent and that said Letters Patent is hereby corrected as shown below:

On the Title Page:
Item 56, U.S .PATENT DOCUMENTS, should include the following references:

| | | | |
|---|---|---|---|
| 3,893,447 | 7/1975 | Hochheimer et al. | 600/431 |
| 4,198,144 | 4/1980 | Matsumura et al. | 396/18 |
| 4,920,371 | 4/1990 | Kaneko, Kiyotaka | 396/189 |
| 4,854,691 | 8/1989 | Sekine et al. | 351/221 |
| 4,933,756 | 6/1990 | Sekine | 358/93 |
| 4,960,327 | 10/1990 | Sekine | 351/221 |
| 4,989,023 | 1/19991 | Sakurai et al. | 354/62 |
| 5,042.939 | 8/1991 | Zayek | 351/206 |
| 5,066,116 | 11/1991 | Sekine | 351/221 |
| 5,140,352 | 8/1992 | Moore et al. | 354/62 |
| 5,181,055 | 1/1993 | Sano et al. | 354/62 |
| 5,214,454 | 5/1993 | Sano | 351/206 |
| 5,237,356 | 8/1993 | Ohtsuka | 354/62 |
| 5,247,318 | 9/1993 | Suzuki | 351/213 |
| 5,252,821 | 10/1993 | Sugimura | 250/22 |
| 5,255,026 | 10/1993 | Arai et al. | 351/206 |
| 5,270,924 | 12/1993 | Hideshima | 364/413.13 |
| 5,287,129 | 2/1994 | Sano et al. | 351/233 |
| 5,300,964 | 4/1994 | Kobayashi | 351/207 |
| 5,315,329 | 5/1994 | McAdams | 351/206 |
| 5,394,199 | 2/1995 | Flower | 351/206 |
| 5,400,791 | 3/1995 | Schlier et al. | 128/664 |
| 5,437,274 | 8/1995 | Khoobehi et al. | 128/633 |
| 5,543,865 | 8/1996 | Nanjo | 351/206 |
| 5,557,349 | 9/1996 | Yoneya et al. | 351/206 |
| 5,557,321 | 9/1996 | Kohayakawa et al. | 348/78 |
| 5,572,266 | 11/1996 | Ohtsuka | 396/18 |
| 5,617,156 | 4/1997 | Sano et al. | 351/214 |
| 5,668,621 | 9/1997 | Nanjo | 351/206 |
| 5,742,374 | 4/1998 | Nanjo et al. | 351/206 |
| 5,745,163 | 4/1998 | Nakamura et al. | 348/46 |
| 5,830,147 | 11/1998 | Feke et al. | 600/479 |

UNITED STATES PATENT AND TRADEMARK OFFICE
CERTIFICATE OF CORRECTION

PATENT NO. : 6,983,106 B2
APPLICATION NO. : 10/162429
DATED : January 3, 2006
INVENTOR(S) : Van Houten It is certified that error appears in the above-identified patent and that said Letters Patent is hereby corrected as shown below:

<u>On the Title Page:</u> (cont'd)
Item 56, U.S .PATENT DOCUMENTS, should include the following references:
    6,158,864   12/2000        Masuda et a.         351/206

Signed and Sealed this

Seventeenth Day of April, 2007

JON W. DUDAS
*Director of the United States Patent and Trademark Office*